US008496834B2

(12) United States Patent
Carr et al.

(10) Patent No.: US 8,496,834 B2
(45) Date of Patent: Jul. 30, 2013

(54) PROCESS FOR FRACTIONATING A MIXTURE OF POLYISOCYANATES

(75) Inventors: Robert Carr, Bertem (BE); Rabah Mouazer, Wavre (BE); Ivo Frans Johanna Vankelecom, Blanden (BE); Angels Cano Odena, Leuven (BE)

(73) Assignee: Huntsman International LLC, The Woodlands, TX (US)

( * ) Notice: Subject to any disclaimer, the term of this patent is extended or adjusted under 35 U.S.C. 154(b) by 599 days.

(21) Appl. No.: 12/679,918

(22) PCT Filed: Sep. 2, 2008

(86) PCT No.: PCT/EP2008/061525
§ 371 (c)(1),
(2), (4) Date: Apr. 22, 2010

(87) PCT Pub. No.: WO2009/040219
PCT Pub. Date: Apr. 2, 2009

(65) Prior Publication Data
US 2010/0213126 A1 Aug. 26, 2010

(30) Foreign Application Priority Data
Sep. 28, 2007 (EP) ..................................... 07117508

(51) Int. Cl.
*B01D 61/02* (2006.01)
*B01D 11/04* (2006.01)
*B01D 11/00* (2006.01)
*C07C 249/14* (2006.01)

(52) U.S. Cl.
USPC ........... 210/651; 210/653; 210/638; 210/644; 560/352

(58) Field of Classification Search
USPC ................. 210/644, 634, 638, 639, 643, 650, 210/651, 653; 560/352
See application file for complete search history.

(56) References Cited

U.S. PATENT DOCUMENTS

| | | | | |
|---|---|---|---|---|
| 3,114,474 A * | 12/1963 | Davis | ............... | 221/92 |
| 3,144,474 A | 8/1964 | Kantyka et al. | | |
| 3,987,075 A * | 10/1976 | Schnabel | ............... | 560/352 |
| 4,372,891 A * | 2/1983 | Hilbert et al. | ............... | 560/352 |
| 5,179,227 A | 1/1993 | Ishida et al. | | |
| 6,180,008 B1 * | 1/2001 | White | ............... | 210/500.39 |
| 6,433,219 B1 | 8/2002 | Strofer et al. | | |
| 7,129,312 B1 | 10/2006 | Krebs et al. | | |
| 7,253,321 B2 | 8/2007 | Hagen et al. | | |
| 2003/0233013 A1 | 12/2003 | Lokum et al. | | |
| 2006/0135810 A1 | 6/2006 | Wolfert et al. | | |
| 2007/0015940 A1 | 1/2007 | Pennemann et al. | | |
| 2007/0117997 A1 | 5/2007 | Keggenhoff et al. | | |

FOREIGN PATENT DOCUMENTS

| | | |
|---|---|---|
| DE | 19804915 | 8/1999 |
| DE | 102005053065 * | 5/2007 |
| EP | 0482490 | 4/1992 |
| EP | 1518874 | 3/2005 |
| EP | 1616890 | 1/2006 |
| WO | WO 00/06293 | 2/2000 |
| WO | WO 01/40342 | 6/2001 |
| WO | WO-2006/022641 * | 3/2006 |
| WO | WO 2006/022641 | 3/2006 |
| WO | WO 2006/130405 | 12/2006 |
| WO | WO-2007/051740 * | 5/2007 |
| WO | WO 2007/051740 | 5/2007 |

OTHER PUBLICATIONS

English language machine translation of description of DE 1020050536065.*
English language machine translation of claims of DE 1020050536065.*
Angels Cano-Odena, Robert H. Carr, Rabah Mouazer, and F.J. Vankelecom; Towards a Process for the Reduction of Monomer Content in MDI-Bsaed Prepolymers; Organic Process Research & Development 2010, 14 (2), 375-379.*
H. J. Twitchett, "Chemistry of the Production of Organic Isocyanates", *Chem. Soc. Rev.* 3(2), 209-230, 1974.
Moore, William M., "Methylenedianiline", *Kirk-Othmer Encyclopedia of Chemical Technology*, 3rd Ed., vol. 2, 338-348 (1978),John Wiley & Sons, New York.
Avdonin, Yu. A., Kulikova, V. A., Pogodin, N. A. "Removal of Insoluble Impurities from Diphenylmethane Diisocyanate by Means of Membranes", *Khimicheskaya Promyshlennost*, vol. 7, 403-404 (1985), Moscow, Russian Federation.
White, Lloyd S. "Transport Properties of a polyimide solvent resistant nanofiltration membrane" *Journal of Membrane Science* vol. 205 191-202 (2002).

* cited by examiner

*Primary Examiner* — David C Mellon
*Assistant Examiner* — Pranav Patel
(74) *Attorney, Agent, or Firm* — Robert A. Diaz

(57) ABSTRACT

Method of fractionating a mixture of polyisocyanates in the liquid phase, optionally in the presence of a suitable solvent or mixture of two or more solvents, by means of a selectively permeable membrane into a permeate stream and a retentate stream of polyisocyanate compositions different to each other and different to the original mixture.

19 Claims, No Drawings

PROCESS FOR FRACTIONATING A MIXTURE OF POLYISOCYANATES

CROSS REFERENCE TO RELATED APPLICATIONS

This application is the National Phase of International Application PCT/EP2008/061525 filed Sep. 2, 2008 which designated the U.S. and which claimed priority to European (EP) Pat. App. No. 07117508.7 filed Sep. 28, 2007. The noted applications are incorporated herein by reference.

The present invention relates to a method of fractionating a mixture of polyisocyanates in the liquid phase.

Polyisocyanates are industrially important chemicals with a wide variety of uses, especially as major components of the vast range of polyurethane-based materials which find multifarious and diverse applications in the modern world.

The major aromatic isocyanates in terms of production volume are the well-known TDI and PMDI. Tolylene di-isocyanate (TDI) is conventionally produced by phosgenation of toluene diamine (TDA), often but not exclusively as the "80:20" mixture of the 2,4' and 2,6' isomers, whose major use is in the field of flexible polyurethane foam. Polymeric methylene di-isocyanate (PMDI) is a complex mixture of polyisocyanates, formed by phosgenation of the corresponding polyamine mixture which, in turn, is produced by the well-known acid-catalysed condensation of aniline with formaldehyde.

PMDI itself is an industrially important isocyanate for producing rigid polyurethane foams which are preferably used as insulation material in the building industry, as insulating foam in the refrigeration appliance industry and as sandwich panel construction material. Often, part of the diphenylmethane 4,4'-diisocyanate, known as MMDI, present in the PMDI, is recovered by means of a suitable technological operation such as distillation or crystallization. MMDI is in turn an important constituent of polyurethane formulations for compact, microcellular and cellular polyurethanes such as adhesives, coatings, fibers, elastomers and integral skin foams. Likewise, various mixtures of the diisocyanate isomers in varying proportions (so-called "Mixed Isomer" products) can be prepared. Accordingly, the term "PMDI" as used herein encompasses PMDI mixtures in which monomeric MDI, for example 4,4'-, 2,2'- and/or 2,4'-MDI, is present. Generally "MDI" is used herein to denote any of the various materials derived from PMDI such as PMDI itself, di-isocyanate isomer mixtures and pure or essentially-pure di-isocyanate isomers.

Aliphatic polyisocyanates such as isophorone diisocyanate (IPDI) and hexamethylene diisocyanate (HDI) are typically produced by phosgenation of the corresponding polyamines, although significant efforts have been made to produce these products by non-phosgene processes.

Many further isocyanates are known such as R,S-1-phenylethyl isocyanate, 1-methyl-3-phenylpropyl isocyanate, naphthyl diisocyanate (NDI), n-pentyl isocyanate, 6-methyl-2-heptane isocyanate, cyclopentyl isocyanate, 2,4- and 2,6-diisocyanatomethylcyclohexane (H6TDI) and the isomer mixtures thereof, o-, m- or p-xylene diisocyanate (XDI), diisocyanatocyclohexane (t-CHDI), di(isocyanatocyclohexyl)methane (H12MDI), tetramethyl-m-xylylene diisocyanate (m-TMXDI), 1,3-bis(isocyanatomethyl)cyclohexane (H6XDI), 1,6-diisocyanato-2,2,4,4-tetramethylhexane, 1,6-diisocyanato-2,2,4-trimethylhexane and mixtures thereof (TMDI).

Considering commercial scale production, phosgenation is by far the most significant method of manufacturing aliphatic and aromatic polyisocyanates and is typically carried out by reaction of the corresponding polyamines with phosgene, usually in the presence of a process solvent selected from the range of hydrocarbons, halohydrocarbons, ethers, esters and the like. Monochlorobenzene (MCB) and ortho-dichlorobenzene (ODCB) are often used.

In all cases, the product of the phosgenation reactions (after removal of excess phosgene, hydrogen chloride and the process solvent by various methods well-known to those skilled in the art) is a crude mixture of the desired polyisocyanate and various by-products. The by-products typically also have isocyanate functional groups and are thus also a type of polyisocyanate compound or mixtures containing polyisocyanate compounds. In the case of TDI, the desired polyisocyanate is itself typically a mixture of the 2,4' and 2,6' TDI isomers which is removed by known means from polyisocyanate reaction byproducts. Likewise, for aliphatic isocyanates, the desired aliphatic isocyanate product is removed by known means from polyisocyanate reaction byproducts. In the case of PMDI, the desired polyisocyanate is itself a mixture of a range of molecular weight homologues, each with a number of isomeric forms, all of which are thus polyisocyanates in which are typically contained the polyisocyanate reaction byproducts.

There exists a wide range of production methods to process the crude reaction mixtures further.

Crude TDI is typically subjected to fractional distillation to produce the desired TDI di-isocyanate product as the distillate and leaving a residue of higher molecular weight materials. The high temperatures required to distill the di-isocyanates inevitably leads to formation of additional higher molecular weight compounds for example due to reaction between the isocyanate funtional groups. A non-limiting example is formation of carbodiimides and, subsequently, uretonimines. The compounds termed carbodiimides and uretonimines also have isocyanate functional groups and are thus also polyisocyanates. Many process variations are described for both the distillation (see for example US 2006/135810 and US 2007/015940) and for further processing of the residue (see for example US 2003/233013). Many of these processes are also applicable in general terms to the manufacture of aliphatic polyisocyanate although specific process variations such as temperatures, pressures, etc. will be tuned to the specific properties of the target product, for example the volatility, by those skilled in the art.

Crude PMDI is also often first subjected to a fractional distillation, usually comprising a partial removal of some of the di-isocyanates to produce a mixture of di-isocyanate isomers as the distillate and leaving a bottom product which is a mixture. Many process variations are described (see for example US 2007/117997, EP 1518874, WO 2006/022641, WO 2007/051740). The bottom product is a mixture containing di-isocyanates, tri-isocyanates, tetra-isocyanates, etc. and molecules containing other functional groups such as ureas, biurets, uretidiones, isocyanurates, carbodiimides, uretonimines, etc. some of which are produced in the distillation step itself. Although containing such functional groups, these latter compounds also contain isocyanate groups and are thus also polyisocyanates.

As well as generation of additional higher molecular weight impurities, distillation requires use of complex equipment and significant energy and thus is problematic at commercial scale both in terms of loss of —NCO yield, change of product quality, process operational complexity and process costs.

PMDI contains reaction by-products which can affect the properties of the polyisocyanate mixture itself and especially the properties of derived products such as polyurethane foams. These properties include but are not limited to the polyisocyanate reactivity, the compatibility of the polyisocyanate with the polyol, the colour of the polyisocyanate and the color of the derived foam. Methods to separate the product into fractions using solvents exist (for example U.S. Pat. No. 3,144,474 and U.S. Pat. No. 3,987,075). These methods are also applicable to the purification of crude reaction mixtures in the production of TDI and other polyisocyanates. Problems are use of additional chemicals at large scale for commercial operation, resulting in additional complexity for the production process both in terms of the separation step and subsequent recovery of the desired product and separation and reuse, with optional purification, of the solvents. Significant extra processing costs are also inherent to such an approach.

The PMDI bottom product resulting after partial removal of a portion of the di-isocyanates, either by fractional distillation or other means, is a mixture. The exact composition of this mixture is dependent on the composition of the corresponding polyamine mixture, the amount of di-isocyanate removed and exact conditions of the various process stages and the amounts of various impurity species formed there. The composition of the polyamine mixture can be varied by many and varied means known to those skilled in the art and comprises especially of variations in the aniline-formaldehyde ratio, the type and amount of acid catalyst used, the temperatures used in the various stages of the process and the type and configuration of the process and process equipment. The continuous, discontinuous, or semi-continuous preparation of di- and polyamines of the diphenylmethane series, called PMDA is described in numerous patents and publications [see, for example JP 9406590, DE 19804915, EP 1616890 and references therein and also H. J. Twitchett, Chem. Soc. Rev. 3(2), 209 (1974), M. V. Moore in: Kirk-Othmer Encycl. Chem. Technol., 3rd ed., New York, 2, 338-348 (1978)]. Despite such variation however, there remain accessible only certain mixtures of polyisocyanate homologues and related isomer compositions which can be produced by economically feasible means. It is likely that other compositions, if accessible, would find particular beneficial uses in one or more applications which could be polyurethane, polyurea or any of the other product areas where polyisocyanates are beneficially employed.

The distilled MDI di-isocyanate isomer mixture can be used as such or can be further fractionated by any well-known means or combinations of means (fractional distillation, fractional crystallisation, partial crystallisation and filtration, etc.) to produce products with a range of di-isocyanate isomer compositions.

Prepolymers containing for example urethane groups and terminal isocyanate groups are important intermediates for the production of polyurethanes. These are frequently based on diisocyanates but may contain one or more additional isocyanates. Such prepolymers are well-known and are widely described in the literature. They are typically prepared by reacting compounds having at least two hydrogen atoms which are reactive towards isocyanate groups, in particular polyols, with an excess of polyisocyanates. The urethane reaction of the at least bifunctional isocyanate with the at least bifunctional polyol also forms oligomeric products beyond the stoichiometric reaction product, since each intermediate contains reactive NCO or OH groups which can in turn react further with starting materials or other intermediates which have already been formed. The formation of such oligomeric polyurethanes is undesirable when, for example, defined A-B-A structures of isocyanate and polyol are to be built up. Such defined structures have a positive effect on the property profile of foamed and compact elastomers such as thermoplastic polyurethanes or pourable elastomers. Furthermore, the prepolymer viscosity generally increases with the degree of polymerization. Highly viscous prepolymers generally restrict further processing, especially in 2-component systems, to a considerable extent, since the miscibility of isocyanate and polyol components is impaired. The reaction products present in these so-called prepolymers also have isocyanate functional groups and are thus also polyisocyanates.

In the preparation of the prepolymers containing isocyanate groups, unreacted monomers of the diisocyanate used in excess usually remain in the prepolymer regardless of the reaction time. This residual content of monomeric diisocyanate can cause problems in the use of isocyanate prepolymers or in their further processing. Thus, some of the monomers, for example tolylene diisocyanate (TDI) or the aliphatic diisocyanates hexamethylene 1,6-diisocyanate (HDI) and isophorone diisocyanate (IPDI) have an appreciable vapor pressure even at room temperature and therefore have a toxic effect, particularly in spray applications due to the isocyanate vapors occurring there. In use at elevated temperatures as are frequently necessary, for example, in the processing of adhesives, the isomers of diphenylmethane diisocyanate (MDI) also form aerosol or gaseous emissions. Since costly measures for maintaining the purity of, in particular, air breathed in are generally prescribed by law to protect a person carrying out the processing, the user has an interest in diisocyanate-free prepolymers or prepolymers with significantly reduced levels of diisocyanates. Furthermore, monomeric diisocyanates themselves or in the form of their reaction products with amines can in the presence of moisture form "migrates" which migrate in an undesirable manner from the finished polyurethane product to its surface and from there, as in the case of vehicle interiors, into the ambient air or, as in the case of packaging films, into the product which has been packed. In addition, monomeric MDI tends to crystallize in the prepolymer.

In the case of conventional prepolymers which still contain significant amounts of monomeric diisocyanate, the product properties, for example the viscosity, are determined predominantly by the unreacted, free diisocyanate. However in the case of polyurethane prepolymers having a low or significantly reduced content of free diisocyanate, for example on the basis of tolylene diisocyanate (TDI) or diphenylmethane diisocyanate (MDI), as are now demanded by the market, the formation of oligomeric products has a substantial influence on the product viscosity and other polymer-physical parameters of the system. The opportunity of carrying out a controlled reaction to control the degree of polymerization would be particularly desirable for the latter cases. The product distribution in the prepolymer is influenced decisively by the molar ratio of the starting materials to one another. Thus, the groups which can undergo an addition reaction have to be present in close to equimolar amounts in order to achieve high molecular weights. The result is broad molecular weight distributions having a low molar proportion of the individual fractions. However, the large molar excess of monomeric diisocyanate remaining in the product may then have to be removed again, which costs money. The use of high molar excesses of free isocyanate should therefore be avoided where possible. Reduction of the amount of monomeric diisocyanate can be achieved by distillation [as described for example in EP 1518874] or by solvent extraction or precipitation and filtration of solids [as described for example in WO 01/40342]. However, such approaches also impart significant extra complexity and hence cost to the production process.

A further possible way of suppressing the formation of relatively high molecular weight adducts in the preparation of the prepolymers is the use of diisocyanates having isocyanate groups of differing reactivity. Common, commercially available examples of such diisocyanates, hereinafter referred to as unsymmetrical diisocyanates, are 2,4-TDI, 2,4'-MDI and IPDI. However, such an approach is obviously limiting to the use of only certain isocyanates.

A further possible way of suppressing the formation of relatively high molecular weight adducts in the preparation of the prepolymers is the use [see US 2007/060731] of unsymmetrical diisocyanates, in particular 2,4-TDI, 2,4'-MDI and/ or IPDI, as diisocyanates, carrying out the reaction in the presence of organometallic catalysts, then removing these organometallic catalysts from the reaction product or deactivating them and subsequently separating off excess monomeric diisocyanate from the reaction product. This is clearly a complex approach imparting significant costs to the production of prepolymers with reduced levels of monomeric diisocyanates.

Isocyanate variants (for example, isocyanate products subjected to further specific reactions to produce for example reaction products containing uretonimine or isocyanurate or biuret functional groups and the like) are well known and widely used. The reaction products present in these so-called variants also have isocyanate functional groups and are thus also polyisocyanates. Production of products with reduced levels of the lowest molecular weight polyisocyanates for example monomeric MDI are desirable as in the case of prepolymers described above.

Problems for the production of monomer-free variants or variants with significantly reduced levels of monomeric diisocyanates, for example by distillation are similar to those encountered in the preparation of prepolymers and include formation of additional higher molecular weight species, usually with accompanying viscosity increases.

Thus, there remains a clear need for a separation process applicable for the treatment of various polyisocyanate mixtures which does not produce significant quantities of new components and which is economically beneficial in terms of relatively simple process equipment and relatively low operating costs in which an original polyisocyanate mixture is fractionated into at least two polyisocyanate streams with different compositions. It has now surprisingly been found that such need can be provided by the use of a process employing membranes.

For example, we have surprisingly found that a PMDI feed composition can be fractionated by means of membrane based processes into two PMDI's with distinctly different compositions.

For example, we have also found that the amount of free diisocyanate in MDI based prepolymers can be significantly reduced by means of membrane based processes.

Thus, the present invention relates to a method of fractionating a mixture of polyisocyanates in the liquid phase, optionally in the presence of a suitable solvent or mixture of two or more solvents, by means of a selectively permeable membrane into a permeate stream and retentate stream of compositions different to each other and different to the original mixture. The process of the present invention further comprises the steps of recovering the permeate (which passes through the selectively permeable nanofiltration membrane) and the retentate (which is retained by the selectively permeable nanofiltration membrane). Where the process includes the use of one or more solvents, the process of the present invention also includes recovery and optional purification and re-use of the solvent by various means including distillation, evaporation and the like, or also using membrane-based processes such as pervaporation.

Solvents for use in the present method can be aromatic hydrocarbons such as benzene, halogenated aromatic hydrocarbons such as monochlorobenzene, o-dichlorobenzene, trichlorobenzene or 1-chloro naphthalene, alkylated aromatic hydrocarbons like toluene, xylene, ethylbenzene, cumene or tetrahydronaphthalene, other functionalised aromatic hydrocarbons such as anisole, diphenylether, ethoxybenzene, benzonitrile, 2-fluoroanisole, 2,3-dimethylanisole, trifluorotoluene, alkanes such as n-pentane, n-hexane, n-heptane or higher branched alkanes, cyclic alkanes like cyclopentane, cyclohexane or derivatives thereof, halogenated alkanes like chloroform, dichloromethane, carbon tetrachloride and alkanes with other functional groups like diethylether, acetonitrile, propionitrile, dioxane and the like, ketones such as acetone and methyl ethyl ketone, amides such as N,N'-dimethyl formamide and N, N'-dimethylacetamide and esters such as ethylacetate and ethylbenzoate, N-methyl-2-pyrrolidone, dimethyl sulfoxide, sulfolane, pyridine and the like or any solvents previously described in the prior art used for the production or processing of isocyanate or isocyanate-containing compounds.

Further individual aspects of the present invention are described below but all of these can be used with additional further non-limiting aspects including carrying out the fractionation optionally in the presence of a suitable solvent or mixture of two or more solvents. In the case of use of one or more solvents, the process optionally includes one or more steps for separation and recovery of the desired products, separation and recovery with optional purification of the solvent or solvents by any suitable means exemplified but not limited to fractional distillation, fractional crystallisation or a further membrane-based separation step. Further variations to the various embodiments are the use of pre-filter or other systems to protect the membranes from deposition of solids, regular or irregular back-flushing of the membrane using polyisocyanates or solvents or gas, optional heating or cooling of liquid streams and various configurations of membranes well-known to those skilled in the art (for example cross-flow systems, dead end systems, spiral wound membranes, hollow-fibre membranes, flat sheet membranes, etc.). The process may be performed in a continuous, semi-continuous or discontinuous (batch mode) manner.

In one aspect the present invention provides a process for the complete or partial separation of di-isocyanates from the crude reaction mixture existing after conversion of the corresponding polyamine mixture, optionally produced by a phosgenation process.

A further aspect of the present invention provides a process for the complete or partial separation of aromatic di-isocyanates from the crude reaction mixture existing after conversion of the corresponding polyamine mixture, optionally produced by a phosgenation process.

A further aspect of the present invention provides a process for the complete or partial separation of TDI di-isocyanates from the crude reaction mixture existing after conversion of the corresponding polyamine mixture, optionally produced by a phosgenation process.

A further aspect of the present invention provides a process for the complete or partial separation of aliphatic di-isocyanates from the crude reaction mixture existing after conversion of the corresponding polyamine mixture, optionally produced by a phosgenation process.

A further aspect of the present invention provides a process for the complete or partial separation of MDI di-isocyanates from the crude reaction mixture existing after conversion of the corresponding polyamine mixture, optionally produced by a phosgenation process.

A further aspect of the present invention provides a process for the separation of the crude reaction mixture existing after conversion of the corresponding polyamine mixture, optionally produced by a phosgenation process, into a permeate PMDI stream and a retentate PMDI stream of differing compositions. Each individual or both of the PMDI mixtures so produced may be a completely novel polyisocyanate mixture, because they cannot be prepared according to the prior art.

A further aspect of the present invention provides a process for the separation of the crude reaction mixture existing after conversion of the corresponding polyamine mixture, optionally produced by a phosgenation process, into a retentate PMDI stream and a permeate stream consisting of di-isocyanates or a mixture of di-isocyanates and tri-isocyanates.

A further aspect of the present invention provides a process for the complete or partial separation of MDI di-isocyanates from a polyisocyanate mixture composed of MDI and higher molecular weight compounds previously produced by reaction of MDI or PMDI with mono- or polyfunctional compounds or mixtures thereof (so called Prepolymers) or by further chemical treatment of MDI or PMDI by known processes (so-called Variants). Non-limiting examples of such higher molecular weight compounds include those derived by reaction of the isocyanates with so-called "active H" functional groups such as —OH, NH, $NH_2$, SH, etc. (including polyether polyols, polyester polyols, thiols, polyamines, etc.) and those derived from polyisocyanates by well known chemical transformations (including uretonimines, biurets, isocyanurates, etc.). A further aspect of the present invention provides a similar process where the isocyanate component is an aromatic isocyanate other than MDI or PMDI, for example TDI, or an aliphatic isocyanate for example HDI or a species derived from a lower molecular weight aliphatic isocyanate for example trimerised HDI.

Frequently, in a lot of the above described embodiments the permeate stream will have a lighter colour than the initial feed material and/or the retendate stream.

Since the present invention involves liquid-liquid fractionation, it does not include processes for the simple filtration of solid impurities from polyisocyanates [e.g. Yu. A. Avdonin; V. A. Kulikova; N. A. Pogodin, Khimicheskaya Promyshlennost (Moscow, Russian Federation) (1985), 7, 403-4] nor precipitation of fractions of polyisocyanate mixtures, optionally by use of solvents, followed by simple filtration of the resulting solids from the liquid phase (described, for example, in, U.S. Pat. No. 3,144,474, WO 01/40342 and WO 2007051740) which adds significant process complexity and which is only applicable to a very small number of special situations.

Non-limiting examples of selectively permeable membranes include polymeric membranes, inorganic and ceramic membranes and composite membranes composed of more than one material. Such membranes may by symmetric or asymmetric. The membrane of the present invention can be configured in accordance with any of the designs known to those skilled in the art, such as spiral wound, plate and frame, shell and tube, and derivative designs thereof. The membranes may be of cylindrical or planar geometry. The rejection performance of the membrane may be improved by pre-soaking the membrane in one or more solvents or a polyisocyanate or mixture of polyisocyanates. The performance of the membrane may be improved by pre-treatment with a low molecular weight aromatic or aliphatic mono-isocyanate such as phenyl isocyanate or with other reagents (non-limiting examples include alkylsilanes, fluorosilanes, fluoroalkysilanes, etc). The membrane should be stable in the isocyanate or isocyanate solution i.e. retain the required properties for the duration of the required operating lifetime. The notional molecular weight cut-off as typically quoted by means of measurements on one or more solvents or other pure compounds may or may not give some indication of the appropriateness of a particular membrane for a particular application.

The membrane may be formed from or comprises a material selected from polymeric materials suitable for fabricating microfiltration, ultrafiltration, nanofiltration or reverse osmosis membranes, including polyethylene, polypropylene, polytetrafluoroethylene (PTFE), polyvinylidene difluoride (PVDF), polyethersulfone, polyacrylonitrile, polyamide, polyimide, cellulose acetate, and mixtures thereof. The membranes can be made by any technique known in the art, including sintering, stretching, track etching, template leaching, interfacial polymerisation or phase inversion.

Preferred polymeric membranes include those based on polyimide and polydivinylfluoride and commercially-available membranes from Solsep [Apeldoorn, The Netherlands].

Other preferred membranes are ceramic membranes, preferably those that are pre-treated, for example, as described above.

The membrane may be prepared from an inorganic material such as by way of non-limiting example silicon carbide, silicon oxide, zirconium oxide, titanium oxide, or zeolites, using any technique known to those skilled in the art such as sintering, leaching or sol-gel processes.

The membrane may be non-porous and the non-porous, selectively permeable layer thereof may be formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, crosslinked polyether, and mixtures thereof.

The membrane may comprise a reinforcing material selected from an external mesh and support. This is particularly advantageous for homogenous tubes or sheets. Such tubes or sheets may be reinforced to increase their burst pressure, for example by overbraiding tubes using fibres of metal or plastic, or by providing a supporting mesh for flat sheets.

When the membrane comprises a non-porous layer and an additional component, the additional component may be a supporting layer. The supporting layer may be a porous support layer. Suitable materials for the open porous support structure are well known to those skilled in the art of membrane processing. Preferably the porous support is formed from or comprises a material selected from polymeric material suitable for fabricating microfiltration, ultrafiltration, nanofiltration or reverse osmosis membranes, including polyethylene, polypropylene, polytetrafluoroethylene (PTFE), polyvinylidene difluoride (PVDF), polyethersulfone, polyacrylonitrile, polyamide, polyimide, and mixtures thereof. Specific design parameters for the membranes such as average pore size and pore size distribution (however the membrane permeability is created and defined), nominal molecular weight cut-off, thickness of the semi-permeable layer and properties of other layers in the membrane (if present) as well as the additional materials required for and the design of the actual unit containing the membrane can all be determined for the various embodiments by those skilled in the art.

The separation may be by means of a pressure driven membrane process which involves a process of separating two or more components over a membrane by means of a pressure gradient, generated by a means that generates pressure at the feeding site for instance by a means to generate a gas pressure or by a means to generate a mechanical pressure. The process may make use of membranes prepared from filled elastomers.

The separated fractions are by their nature more concentrated in various components of the original mixture and thus can prove to be beneficial for purposes of chemical analysis.

EXAMPLES

Example 1

A solution of 25 wt % of polyimide polymer [Lenzing® P84, Evonik Degussa GmbH, Geb. 1266, PB 14, Paul-Baumann-Str. 1, 45772 Marl, Germany] in N-methyl-pyrrolidine (NMP) was deposited as a coating on a non-woven support [Vildeon FO 2471, Freudenberg, Germany] made from polypropylene/polystyrene material of approximate thickness of 0.18 mm using a casting knife film applicator with the gap set to approximately 250 microns. The membrane was left for about five minutes for solvent evaporation before being removed from the film applicator and immediately immersed in a water coagulation bath at room temperature for fifteen minutes to complete the polymer precipitation. The resulting membrane was stored in isopropyl alcohol (IPA) for 3 hours, then transferred to a IPA/glycerol bath (60:40 volume ratio) for at least 3 days prior to use. The membrane was removed from the IPA/glycerol and soaked in mono-chlorobenzene (MCB) for twenty minutes. The membrane was then mounted in a so-called "dead-end" pressure cell and MCB was flushed through the membrane at 15 bars for at least thirty minutes to ensure that the alcohols were removed.

A sample of a polymeric MDI to be used for the experiment was analysed by gas chromatographic (GC) analysis with flame-ionisation detection. A value of 21 was found for the ratio of di-isocyanates to tri-isocyanates (isomers of each molecular weight added together). A solution of 50 wt % of the polymeric MDI in MCB was fractionated through the membrane in the pressure cell at 6 bar pressure for ninety-five minutes. The di/tri ratio of samples of the permeate and retentate were 37 and 17 respectively, showing clearly that the original feed, the permeate and the retentate were polyisocyanates with distinctly different compositions.

Example 2

A commercial "nanofiltration" membrane with nominal cut-off of 500 Daltons (Solsep® 030305, Solsep bv., Apeldoorn, The Netherlands) was mounted in the pressure cell and MCB was flushed through it as described in Example 1. The same solution of 50 wt % polymeric MDI in MCB as used in Example 1 was fractionated through the membrane at 14 bar pressure for eighty minutes. The di/tri ratio of samples of the permeate and retentate as determined by GC analyses were 64 and 18 respectively, showing clearly that the original feed, the permeate and the retentate were polyisocyanates with distinctly different compositions.

Example 3

A prepolymer formed by reaction of 10.5 wt % commercial grade tripropylene glycol (TPG) with MDI di-isocyanates (containing approximately 50% 4,4'-MDI and 50% 2,4'-MDI) was analysed by Gel Permeation Chromatography (GPC) with UV-detection at 254 nm and the content of di-isocyanates was found to be 24.1 (relative area %) and of higher molecular weight isocyanates [MDI-TPG-MDI species of various MW, isomers and chain-extended species] was found to be 75.9%. The membrane, equipment and procedures as described in Example 1 were used to fractionate a 50 wt % solution of this prepolymer in MCB at 30 bar pressure for 108 minutes. The area % amounts of the di-isocyanates and higher molecular weight isocyanates in the retentate were 20.3 and 79.7 respectively, showing clearly that the di-isocyanate content of the retentate was reduced compared to the feed composition. It was noted that the permeate was lighter in colour than both the initial feed material and the retentate. The collected permeate could be used as such or could also be used as the starting material for further production of the same or a different prepolymer.

Example 4

A uretonimine-modified 4,4'-MDI variant, prepared by a phospholine oxide catalysed process, was analysed by GPC with UV detection at 254 nm and the content of di-isocyanates was found to be 41.1 (relative area %) and of higher molecular weight isocyanates was found to be 58.9%. The equipment and procedures as described in Example 1 were used with a commercial "nanofiltration" membrane (Solsep® 010206, Solsep bv., Apeldoorn, The Netherlands) to fractionate a 50 wt % solution of this prepolymer in MCB at 28 bar pressure for 78 minutes. The area % amounts of the di-isocyanates and higher molecular weight isocyanates in the permeate were 44.3 and 55.7 respectively showing clearly that the compositions of the polyisocyanate mixtures could be changed by membrane-based fractionation.

Example 5

The solution of the MDI-TPG prepolymer in MCB as used in Example 3 was fractionated for 102 minutes at 10 bar according to the procedure described in Example 2, using the commercial membrane with a nominal cut-off of 500 Daltons (Solsep® 030305, Solsep bv., Apeldoorn, The Netherlands). The ratio of the MDI di-isocyanates to higher MW polyisocyanates of samples of the initial, permeate and retentate as determined by GPC analyses were 0.31, 0.93 and 0.28 respectively, showing clearly that the original feed, the permeate and the retentate were polyisocyanates with distinctly different compositions.

Example 6

A prepolymer consisting of 56% (by weight) of 4,4'-MDI, 6% of the uretonimine-modified variant described in Example 4, 1% of triphenyl phosphite and 37% of a polyester formed from ethylene glycol, 1,4-butanediol and adipic acid (nominal MW of 2000) was analysed by GPC and a value of 1.24 was found for the ratio of the 4,4'-MDI to higher MW polyisocyanates. A solution of this prepolymer in MCB was fractionated for 140 minutes at 20 bar using the procedure and membrane described in Example 5. GPC analyses of the permeate and the retentate showed the compositions to be significantly different to the original prepolymer, the ratios of 4,4'-MDI to higher MW polyisocyanates being 8.1 and 1.0 respectively.

Example 7

The uretonimine-modified variant described in example 4 was used without dilution in solvent in a fractionation experiment with the Solsep® 030305 membrane as used as in the examples 2, 5 and 6. The test was performed for 50 minutes at a pressure of 40 bar. The ratios of di-isocyanate to higher MW polyisocyanates for the initial sample, the permeate and the retentate were 0.73, 4.06 and 0.66 respectively.

Example 8

A prepolymer formed from 89.5 wt % of di-isocyanate isomers (4,4'-MDI to 2,4'-MDI circa 70:30) reacted with 10.5 wt % of commercial-grade tri-propylene glycol (TPG) was analysed by GPC and a value of 25.34% (area %) was found for the di-isocyanates and 74.66% (area %) for the higher molecular weight polymers. This undiluted prepolymer was fractionated through the Solsep® 030305 membrane in the pressure cell at 40 bar pressure at 66° C. for 100 minutes. The ratio of di-isocyanates to higher MW polyisocyanates obtained for the permeate and the retentate were 3.99 and 0.31 respectively.

Example 9

A membrane was made using a solution of 21 wt % of polyimide polymer (polyimide P84® from HP Polymer Inc., 1702 S. Hwy. 121, Suite 607-177, Lewisville, Tex. 75067, USA), 47.4 wt % NMP and 31.6 wt % THF as described in Example 1. A prepolymer formed by reaction of polymeric MDI with 0.57 wt % of a commercial-grade tri-propylene glycol (TPG) and 22.95 wt % of polypropylene glycol (PPG2000) was analyzed by GPC and a value of 0.41 was found for the ratio of the di-isocyanates to higher MW polyisocyanates. A 50 wt % solution of this prepolymer in MCB was fractionated at room temperature for 120 minutes at 45 bars using the procedure described in Example 1. GPC analyses of the permeate and the retentate showed the compositions to be significantly different to the original prepolymer, the ratios of di-isocyanates to higher MW polyisocyanates being 3.71 and 0.39 respectively.

Example 10

A membrane was made using a solution of 21% of polyimide polymer P84 (HP Polymer Inc.) and 63.2% NMP as described in Example 1. The prepolymer solution described in Example 9 was fractionated at room temperature for 125 minutes at 45 bar according to the procedure described in Example 1. GPC analyses of the permeate and the retentate showed the compositions to be significantly different to the original prepolymer, the ratios of di-isocyanates to higher MW polyisocyanates being 2.80 and 0.38 respectively.

Example 11

A solution of 1% of phenyl isocyanate in acetone was permeated through a commercially-available ceramic membrane [silanized zirconia membrane from HITK, address Hermsdorfer Institut für Technische Keramik e.V., Michael-Faraday-Str. 1, 07629 Hermsdorf/Thuringia, Germany] for 8 hours, after which the membrane was left soaking in the solution for a further 16 hours. The membrane was then flushed thoroughly with acetone and dried. The membrane was then mounted in a cross-flow pressure cell equipped with a feed vessel, high pressure pump, receiver vessel, heat exchanger unit and various connecting lines, recycle lines, sensors, etc. [flow, temperature, pressure]. Before starting the experiment, the setup and the membrane were flushed twice with 10 litres of polymeric MDI for about half an hour at 50° C. and then drained completely.

A sample of polymeric MDI was fractionated through the membrane at 5 bar pressure for two hours at 50° C. The ratio of di-isocyanates to higher MW polyisocyanates obtained for the permeate was 0.58 compared to 0.41 in the original feed. Surprisingly the permeate had an L* colour greater than 60 compared to the original feed which had an L* colour of about 12.

The invention claimed is:

1. A method of fractionating a mixture of polyisocyanates in the liquid phase by means of a selectively permeable membrane into a permeate stream and a retentate stream of polyisocyanate compositions different to each other and different to the mixture of polyisocyanates the original mixture wherein the method of fractionating the fractionation method does not include filtration of solid impurities from the mixture of polyisocyantes.

2. The method according to claim 1 wherein subsequently the permeate stream and the retentate stream are separated and recovered.

3. The method according to claim 1 wherein said fractionation is carried out in the presence of a suitable solvent or mixture of two or more solvents.

4. The method according to claim 3 wherein the solvent is selected from aromatic hydrocarbons, halogenated aromatic hydrocarbons, alkylated aromatic hydrocarbons, other functionalised aromatic hydrocarbons, alkanes, cyclic alkanes, halogenated alkanes and alkanes with other functional groups, ketones, amides and esters, N-methyl-2-pyrrolidone, dimethyl sulfoxide, sulfolane and pyridine.

5. The method according to claim 3 wherein the solvent is purified and reused.

6. The method according to claim 1 wherein the selectively permeable membrane is selected from polymeric membranes, inorganic or ceramic membranes or composite membranes composed of more than one material.

7. The method according to claim 6 wherein the selectively permeable membrane is a polymeric membrane comprising polyimide or polydivinylfluoride.

8. The method according to claim 6 wherein the selectively permeable membrane.

9. The method according to claim 1 wherein the mixture of polyisocyanates originates from conversion of a polyamine mixture using a phosgenation process.

10. The method according to claim 9 wherein the method involves complete or partial separation of di-isocyanates from the original polyisocyanate mixture.

11. The method according to claim 10 wherein the di-isocyanates are aromatic.

12. The method according to claim 1 wherein both the permeate and the retentate stream comprise polymeric methylene di-isocyanate.

13. The method according to claim 1 wherein the method of fractionating the mixture of polyisocyanates involves the fractionation of a reaction mixture existing after conversion of a polyamine mixture, into the retentate stream and the permeate stream with distinctly different compositions.

14. The method according to claim 4 wherein the solvent is recovered.

15. The method according to claim 8 wherein the ceramic membrane has been pre-treated.

16. The method according to claim 11 wherein the di-isocyanates comprises tolylene di-isocyanate or diphenylmethane diisocyanate.

17. The method according to claim 14 wherein the solvent is purified and reused.

18. The method according to claim 13 wherein the reaction mixture is produced by a phosgenation process.

19. The method according to claim 3 wherein the solvent is recovered, purified, and reused.

* * * * *